(12) United States Patent
Timpson

(10) Patent No.: US 7,111,794 B2
(45) Date of Patent: Sep. 26, 2006

(54) STATIC AIR FRESHENER

(76) Inventor: David Timpson, 1735 S. Berry Knoll Blvd., Centennial Park, AZ (US) 86021

( * ) Notice: Subject to any disclaimer, the term of this patent is extended or adjusted under 35 U.S.C. 154(b) by 249 days.

(21) Appl. No.: 10/810,490

(22) Filed: Mar. 27, 2004

(65) Prior Publication Data

US 2005/0077375 A1    Apr. 14, 2005

Related U.S. Application Data

(60) Provisional application No. 60/458,678, filed on Mar. 28, 2003.

(51) Int. Cl.
   *A62C 13/62* (2006.01)
   *A24F 25/00* (2006.01)
   *A61L 9/04* (2006.01)

(52) U.S. Cl. .................... 239/340; 239/34; 239/36; 239/40; 239/41; 239/42; 239/51.5

(58) Field of Classification Search ............... 239/340, 239/34, 36, 40, 41, 42, 51.5, 54, 55, 57
See application file for complete search history.

(56) References Cited

U.S. PATENT DOCUMENTS

| | | | | |
|---|---|---|---|---|
| 2,109,092 | A | * | 2/1938 | Roll .............. 239/36 |
| 2,564,860 | A | * | 8/1951 | Henry ............ 239/54 |
| 4,676,954 | A | | 6/1987 | Wilson |
| 4,802,626 | A | * | 2/1989 | Forbes et al. ....... 239/36 |
| 4,869,407 | A | | 9/1989 | Booth, Jr. et al. |
| 4,993,177 | A | | 2/1991 | Hudson |
| 5,099,752 | A | | 3/1992 | Bosley |
| 5,202,571 | A | | 4/1993 | Hirabayashi |
| 5,312,566 | A | * | 5/1994 | Carroll et al. ..... 261/18.4 |
| 5,314,669 | A | | 5/1994 | Hamilton |
| 5,422,078 | A | * | 6/1995 | Colon ............. 422/123 |
| 5,431,859 | A | | 7/1995 | Tobin |
| 5,527,493 | A | | 6/1996 | McElfresh et al. |
| 5,651,522 | A | | 7/1997 | Davis et al. |
| 5,725,152 | A | | 3/1998 | Akyu |
| D394,602 | S | | 5/1998 | Fernandez |
| 5,823,432 | A | | 10/1998 | Hogan |
| 5,853,672 | A | | 12/1998 | Lorman et al. |
| 6,123,906 | A | | 9/2000 | Farmer |
| D432,023 | S | | 10/2000 | Fox |
| 6,126,085 | A | * | 10/2000 | Wanzenbock ........ 239/36 |
| 6,140,934 | A | | 10/2000 | Lam |
| 6,168,088 | B1 | | 1/2001 | Mobley |
| 6,202,345 | B1 | | 3/2001 | Wokal |

(Continued)

OTHER PUBLICATIONS

Ad Hatters, Inc., 2002 Refreshingly Distinctive Air Fresheners, http://www.littlehats.com/main/index/htm, pp. 1-2.

(Continued)

*Primary Examiner*—Davis Hwu
(74) *Attorney, Agent, or Firm*—Holme Roberts & Owen LLP

(57) ABSTRACT

A static air freshener has a frame formed of or with plastic beads impregnated with a scent or aroma. The rate of release of the scent is controlled by the area of the frame to define the useful life of the air freshener. An insert may be place in a void defined by the frame. The insert has a thematic image that may be correlated to a thematic image on the header card of a bag or sack sized to contain the air freshener for positioning at or on the point of sale device.

6 Claims, 2 Drawing Sheets

U.S. PATENT DOCUMENTS

| | | |
|---|---|---|
| 6,234,118 B1 | 5/2001 | Lahens |
| 6,249,645 B1 | 6/2001 | Smith |
| 6,254,836 B1 | 7/2001 | Fry |
| 6,264,887 B1 | 7/2001 | Farmer |
| D461,885 S | 8/2002 | Jordi |
| 6,446,374 B1 | 9/2002 | Ardiff |

OTHER PUBLICATIONS

Ad Hatters, Inc., 2002 Refreshingly Distinctive Air Fresheners, http://www.littlehats.com/main/scents/htm, 1 Page.

Team Dynamics, Inc., 2001 Team Scents Air Fresheners, http://www.gamefaces.com/estore/teamscents.asp, pp. 1-3.

Ad Hatters, Inc., 2002 Refreshingly Distinctive Air Fresheners, http://www.littlehats.com/main/products/htm, 1 Page.

Ad Hatters, Inc., 2 in 1 Air Freshener, Auto, 1 Page.

The Zeo Store., Complete line of sage and natural air fresheners and deodorizers, http://www.zeocrystal.com/products/html, pp. 1-4.

Ths Sharper Image, Ionic Breeze Air Freshener for Bathrooms & Small Spaces, http://www.sharperimage.com/us/en/catalog/productview.jhtml?pid=18538900, 1 Page.

Home Solutions News, 2001-2002 Air Wick® by Wizard name for Wizard®, http://www.homesolutionsnews.com/rbdocs/us/wizard, 1 Page.

Car Care Products, http://www.citrismagic.com/carcare.html, pp. 1-3.

Air Delights, 2002 Automatic Air Neutralizer High Quality Hygiene Products, http://www.airedelights.com/goto.html, pp. 1-2.

\* cited by examiner

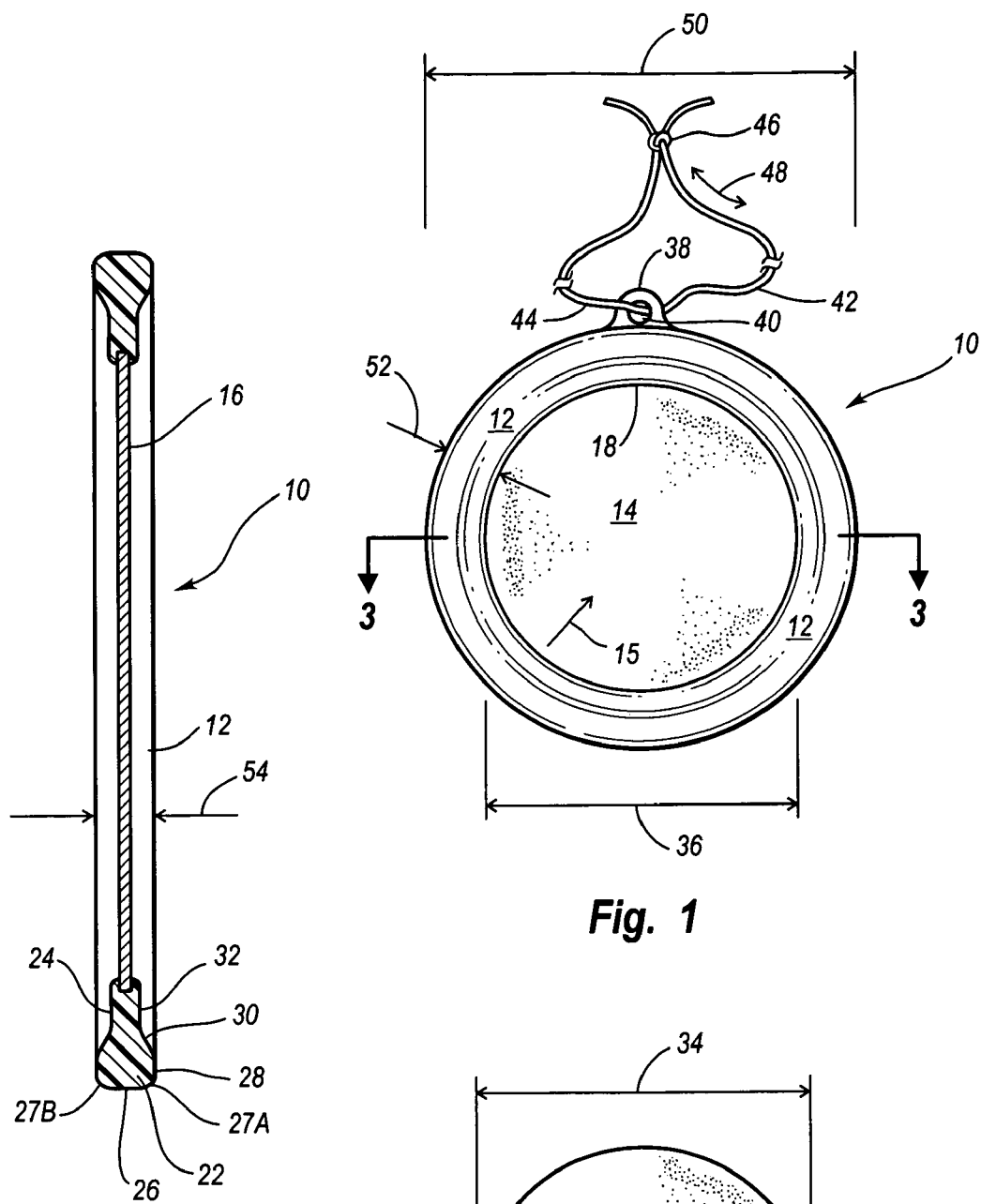
Fig. 1
Fig. 3
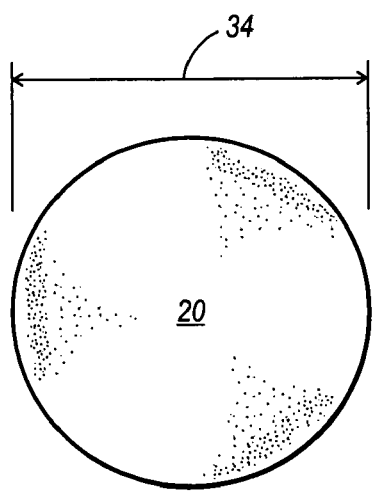
Fig. 2

STATIC AIR FRESHENER

This application claims the benefit of U.S. Provisional Application 60/458,678 filed 28 Mar. 2003.

BACKGROUND OF THE INVENTION

1. The Field of the Invention

The present invention relates to an air freshener for use in a closed vehicle and more particularly to an air freshener with no moving parts and with a selected design theme.

2. Related Art

Air fresheners for use in vehicles are known. They are constructed to release a selected smell, odor or scent into the interior of a closed space (e.g., the passenger compartment of a vehicle) over a particular time or useful life. A wide variety of air fresheners are available which allow the user to select a particular scent and shape.

Typical air fresheners have a scent-containing portion which is inserted into a frame. U.S. Pat. No. 5,823,432 (Hogan) discloses an air freshener in the shape of selected articles of clothing for visual display. U.S. Pat. No. 5,853,672 (Lorman, et al) shows an air freshener that has a fan for stimulating air circulation. The fan is activated when the driver steps on the brakes and is deactivated upon release or removal of the foot from the brake pedal.

Other air fresheners for use in homes of all sizes and shapes are also known. U.S. Pat. Des. No. 461,885 (Jordi) discloses a wall plug air freshener. U.S. Pat. Des. No. 432,023 (Fox) shows a clock air freshener.

Some air fresheners that are static (no moving parts) have a frame and an insert which is made of an absorbing material which is typically a non woven material. That is, the inserts may be made of a porous fiber board which does not accept printed images very well. On porous fiber board, the ink runs so that images are typically blurry. Upon placement of the air freshener in a desired location, the scent, aroma or smell impregnated into the absorbing material migrates into the air so the user may enjoy the scent, aroma or smell. Because such air fresheners cannot accept ink, they in turn are not good substrates for printing images thereon. Further, such air fresheners have a limited life because the amount of scent, aroma or smell that can be impregnated is limited by the thickness and absorption characteristics of the insert.

SUMMARY OF THE INVENTION

A static air freshener has a frame shaped to define a void or a space surrounded by or encompassed by the frame. The frame has at least one side member which is formed from scented plastic beads. A slot or groove is formed in the side member. The slot is oriented toward the space or void. An insert is sized to fit within the void and frictionally engage the slot or groove to retain the insert in the void or space.

Preferably, the insert is made of a non woven material which is substantially rigid. Even more preferably the frame is formed of one side member which is circular in projection. An attachment means may also be attached to or formed with the frame for attaching the static air freshener to a support.

In a preferred configuration, the attachment means includes an eye structure unitarily formed with the frame. The eye structure has an aperture sized to receive a line which may be threaded there through. The line has a length selected for securing the frame to a support.

In an alternate and preferred arrangement an air freshener unit has a bag. The bag has an opening to receive a static air freshener. The bag is foldable to form a crease proximate the opening. The bag is made of a material which inhibits the flow of air there through.

The air freshener unit includes a header card positioned over the crease of the bag and is secured to the bag to hold the crease and thereby form a seal. The header card has a first graphic image formed thereon based on a first theme.

The air freshener unit includes a frame sized for positioning in the bag. The frame is formed from at least one side member and defines a space or void surrounded by the frame there within. The frame is formed from scented plastic beads. A slot is formed in the side member oriented toward the space. An insert is sized to fit to frictionally engage the slot to be retained in the space. The insert has a second graphic image formed thereon selected to express the theme of the first graphic image.

DESCRIPTION OF THE DRAWINGS

FIG. 1 is a planar view of a frame of the air freshener and air freshener unit of the present invention;

FIG. 2 is a planar view of an insert for positioning in the frame of the air freshener and air freshener unit of the present invention;

FIG. 3 is a side cross section of the frame of FIG. 1 taken along the section lines 3—3.

DESCRIPTION OF THE ILLUSTRATED EMBODIMENTS

Figure 4:
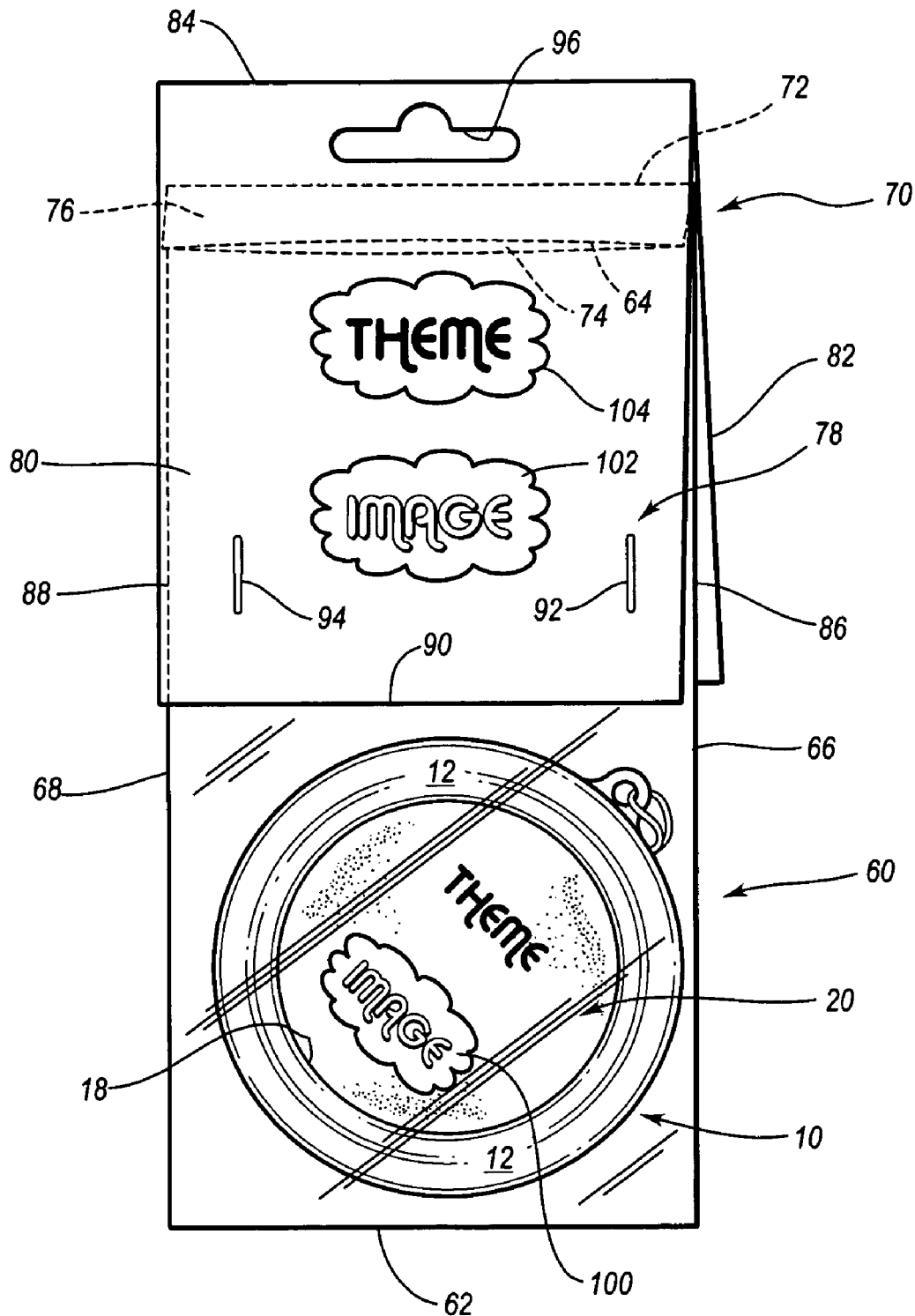
FIG. 4 is a front planar view of an air freshener unit of the present invention.

FIGS. 1 and 3 show a frame 10 formed by a single side member 12. The frame 10 defines a space or void 14 inward or in an interior direction 15 of the side member 12. A slot 16 or groove is formed in the side member 12 about the interior perimeter 18 of the frame 10. An insert 20 is sized to be positioned in the space or void 14 to frictionally engage the slot 16 and thereby be retained in the space or void 14.

The frame 10 is here shown to be formed of one side member 12 that is circular in projection. The frame 10 may also be formed of a plurality of side members configured to define shapes that may in projection, be an oval, a rectangle, a square, an octagon, a triangle, a heart shape, or any other desired geometric shape. The frame 10 may be formed using any suitable system for forming solids from plastic beads including injection molding.

The side member 12 here shown is formed from a scented beaded plastic which is typically either a polyvinylchoride (pvc) or a polyolefin copoly plastic. Suitable plastic beads for this purpose may be purchased from Dyvex Industries, 30 Enterprise Drive, Carbondale, Pa. The scent is added to the plastic and may be any desired scent. For example, one could select scents that to the user produce aromas or a smell much like pine (tree or cone), new car, lilac, rose, or any other desired smell or aroma. When the plastic beads are molded into the side member, the scent, smell or aroma becomes integral therewith. That is, the scent, aroma or smell is made up of molecules that release from the surface of the frame member like frame member 12 to the surrounding atmosphere. Molecules in the interior 22 of the side member migrate toward the exterior surface 24 as the population of molecules proximate the exterior surface 24 move into the atmosphere. With the decreasing population of molecules of scent, aroma or smell, the rate of release to the atmosphere diminishes with time. However, by using scented plastic, the amount of scent, aroma or smell that can be included is increased and the amount that is delivered can be controlled so that the air freshener has a longer useful life. That is, the frame 10 can be suspended in the air and deliver molecules of scent, aroma or smell in sufficient quantity to be detectable by a typical user over a longer period of time in comparison to a comparably sized air freshener that has an impregnated insert within a frame made from something other than scented plastic.

In FIG. 3, it can be seen that the frame member 12 is formed with a base 26. The amount of exterior surface is controlled by shaping the frame member 12 to control the surface area of the exterior surface 24. In turn the amount of aroma, smell or scent that is released over a unit of time is controlled and in turn the useful life of the air freshener. In FIG. 3, it can be seen that the base 26 has arcuate corners 27A and 27B that extend to a shoulder area 28. The shoulder area 28 extends into a groove area 30 and from there to the top area 32. Varying the thickness and shape of the areas will impact on the amount of impregnated material used and in turn the surface area and the release rate.

In FIG. 2, the insert 20 is shown to be circular in cross section and made of a material that is flexible such as a thin cardstock. It is preferably made of high quality cardstock upon which suitable high quality images appear. The insert 20 has a width or diameter 34 which is slightly more than the interior diameter of the space or void 14 so that the insert 20 when positioned in the space or void 14 snugly snaps into the groove 16 formed in the side member 12. While the insert 20 is here shown to be a cardstock item circular in projection, it could be formed in other geometric shapes to fit in the frame of a different geometric shapes. Alternately, the insert 20 could be a decorative item so long as it has at least two legs or feet to frictionally engage the slot 16.

In FIG. 1, attachment means are shown for attaching the air freshener to a support. The attachment means here shown is an eye 38 unitarily formed with the frame member 12. The eye 38 has an aperture 40 sized to receive at least one line 42 and preferably two lines 42 and 44. The two lines 42 and 44 are joined by a knot 46 and have a length 48 selected so that the frame 10 may be suspended or hung from an appropriate support (e.g., a rear view mirror arm). Alternately, the attachment means can include glue, adhesive strips, fasteners (e.g., nails, screws) or any suitable device to hold the air freshener in a desired location for a selected time such as the useful life of the air freshener. Some attachment means may provide for portability or movability of the air freshener from one location to another.

In FIG. 1, the frame 10 has an outside diameter 50 from about 2 inches to about 3 inches and preferably about 2 and ⅝ inches. The side member 12 has a thickness 52 (measured radially) from about ¼ inch to about ½ inch and preferably about ⅜ of an inch. The side member 12 also has a thickness 54 (FIG. 3) from about ⅛ of an inch to about ¾ of an inch and preferably about ¼ of an inch.

The frame 10 of FIG. 3 is shown at about two times its normal size to facilitate illustration.

Turning now to FIG. 4, a frame 10 with an insert 20 is positioned within a bag 60. The bag 60 is here shown to have a bottom 62, a top 64 and two sides 66 and 68. The bag 60 is preferably made of a clear translucent material (e.g., cellophane, clear plastic) which is essentially impervious to the molecules of the scent, aroma or odor in the scented plastic or other material of the air freshener. The bag 60 is folded at or proximate its open end 70 to form a crease 72 which acts as a type of seal to retain air and the scent, aroma or odor there within. That is, the frame 10 of the air freshener with insert 20 is positioned into the interior of the bag 60 through an opening 74 at its open end 70. Once the bag 60 is folded to form the flap 76 and crease 72, the interior of the bag 60 traps some air there in. The scent, odor or smell molecules transfer from the side member 12 to the air in the bag 60; and eventually the partial pressure of air molecules is such that a state of equilibrium is reached so that the frame 10 retains most of its scent, odor or smell.

As seen in FIG. 4, a header card 78 has a front panel 80 and a back panel 82. The two panels are formed from the same card stock and bent at a crease 84. Each panel therefore has effectively a top as the crease 84, two side 86 and 88 and a bottom 90. A portion of the bag 60 and more specifically the crease 72 and flap 76 are positioned between the front panel 80 and back panel 82 and held securely in place as the front panel 80 and back panel 82 are secured to each other by staples 92 and 94. Other forms of securing the front panel 80 and back panel 82 may be used including glue, snaps and the like.

The header card 78 may also have an aperture 96 to facilitate hanging the air freshener unit on a hook. That is, in retail establishments, some goods are positioned on hooks placed on a shelving unit. The header card 78 along with the bag 60 are sized to hang on a hook and be suspended in the space allocated to air fresheners of a typical retail shelf unit.

The insert 20 may be formed from card stock upon which graphics are easily printed. In turn an image 100 appearing on the insert 20 is preferably thematically tied to a similar image 102 appearing on the front panel 80 of the header card 78. A title or thematic statement 104 may appear on the header card 80 as well. Thus a CORVETTE automobile could appear in images 100 and 102 with a thematic statement like CLASSIC CARS appearing thereon. Different classic car images may be used to create a set. Other themes can be used including airplanes, Native American, Off Road or 4 wheeling, swim suit models, athletic teams, and the like. The thematic statement 104 may also be repeated on the insert 20.

What is claimed is:

1. A static air freshener comprising:
   a frame formed from scented plastic beads and shaped to define a void through said frame, said frame being arranged to form a boundary around said void;
   at least one side member formed on said frame;
   a slot formed in said at least one side member, said slot being oriented in said boundary to face toward said void; and
   an insert sized to fit within said void and configured to frictionally engage said slot to retain said insert in said void.

2. The air freshener of claim 1 wherein said insert is made of a non woven material which is substantially rigid.

3. The air freshener of claim 2 wherein said frame is formed of one side member which is circular in projection.

4. The air freshener of claim 1 further including attachment means associated with said frame for attaching said static air freshener to a support.

5. The air freshener of claim 4 wherein said attachment means includes an eye structure unitarily formed with said frame, said eye structure having an aperture sized to receive a line there through, and wherein said attachment means includes a line threaded in said aperture and having a length for securing said frame to a support.

6. An air freshener unit comprising:
   a bag having an opening to receive a static air freshener, said bag being foldable to form a crease proximate said opening, said bag being made of a material to inhibit the flow of air there through;

a header card positioned over said crease and secured to said bag to form a seal, said header card having a first graphic image formed thereon based on a first theme;

a frame positioned in said bag, said frame being formed from at least one side member to define a space there within, and said frame being formed from scented plastic beads;

a slot formed in said at least one side member, said slot being oriented toward said space; and an insert sized to fit within said space and to frictionally engage said slot to retain said insert in said space, said insert having a second graphic image formed thereon selected to express the theme of said first graphic image.

* * * * *